(12) United States Patent
Almstedt et al.

(10) Patent No.: US 10,302,527 B2
(45) Date of Patent: May 28, 2019

(54) METHOD FOR CARRYING OUT A SOUND TEST OF ATLEAST ONE COMPONENT AND ENDOSCOPE DEVICE USED FOR THE SAME

(71) Applicant: SIEMENS AKTIENGESELLSCHAFT, München (DE)

(72) Inventors: Henning Almstedt, Mülheim an der Ruhr (DE); Ralf Bell, Mülheim an der Ruhr (DE); Ulrich Beul, Essen (DE); Kai Brune, Rheinberg (DE); Robin Burzan, Mülheim an der Ruhr (DE); Matthias Heue, Bochum (DE); Benedikt Hofmeister, Mülheim (DE); Mario Koebe, Mülheim an der Ruhr (DE); Michael Löhr, Mülheim an der Ruhr (DE); Stefan Riemann, Kaarst (DE); Andreas Schaarschmidt, Essen (DE); Andreas Ulma, Mülheim an der Ruhr (DE); Sebastian Zahn, Duisburg (DE); Gerta Zimmer, Mülheim an der Ruhr (DE)

(73) Assignee: Siemens Aktiengesellschaft (DE)

( * ) Notice: Subject to any disclaimer, the term of this patent is extended or adjusted under 35 U.S.C. 154(b) by 85 days.

(21) Appl. No.: 15/448,711

(22) Filed: Mar. 3, 2017

(65) Prior Publication Data

US 2017/0261399 A1    Sep. 14, 2017

(30) Foreign Application Priority Data

Mar. 10, 2016  (DE) ................. 10 2016 203 904

(51) Int. Cl.
*G01H 9/00*  (2006.01)
*G01M 7/08*  (2006.01)
(Continued)

(52) U.S. Cl.
CPC ............... *G01M 7/08* (2013.01); *F01D 5/12* (2013.01); *F01D 9/02* (2013.01); *F01D 21/003* (2013.01);
(Continued)

(58) Field of Classification Search
CPC .... G01M 7/08; F01D 5/12; F01D 9/02; F01D 21/003; F01D 25/24; F04D 27/001;
(Continued)

(56) References Cited

U.S. PATENT DOCUMENTS 6,399,939 B1 * 6/2002 Sundaresan ............... G01H 1/12
250/231.1
7,083,384 B2 * 8/2006 Bosselmann ........... G01S 13/50
416/146 R (Continued)

FOREIGN PATENT DOCUMENTS

DE  102006048791 A1  4/2008
DE  102011054596 A1  5/2012
(Continued)

*Primary Examiner* — Lisa M Caputo
*Assistant Examiner* — Nigel H Plumb
(74) *Attorney, Agent, or Firm* — Schmeiser, Olsen & Watts LLP

(57) ABSTRACT

A method is provided for carrying out a sound test for detecting and/or analyzing material faults and/or mounting faults of at least one component, in which the component is excited, by striking, to experience vibrations which generate soundwaves, after which the generated soundwaves are detected and conclusions are drawn about material faults and/or mounting faults on the basis of the detected soundwaves, wherein the striking of the component and the detection of the vibrations are carried out using an endoscope device. In addition, embodiments of the present invention relates to an endoscope device which is configured to carry out the method.

13 Claims, 5 Drawing Sheets

(51) Int. Cl.
| | |
|---|---|
| *F01D 5/12* | (2006.01) |
| *F01D 9/02* | (2006.01) |
| *F01D 21/00* | (2006.01) |
| *F01D 25/24* | (2006.01) |
| *F04D 27/00* | (2006.01) |
| *F04D 29/32* | (2006.01) |
| *F04D 29/52* | (2006.01) |
| *F04D 29/54* | (2006.01) |
| *G01N 29/06* | (2006.01) |
| *G01N 29/265* | (2006.01) |
| *G01N 29/04* | (2006.01) |
| *G01N 29/22* | (2006.01) |
| *G01N 29/44* | (2006.01) |

(52) U.S. Cl.
CPC ........... *F01D 25/24* (2013.01); *F04D 27/001* (2013.01); *F04D 29/324* (2013.01); *F04D 29/522* (2013.01); *F04D 29/542* (2013.01); *G01N 29/045* (2013.01); *G01N 29/0654* (2013.01); *G01N 29/226* (2013.01); *G01N 29/265* (2013.01); *G01N 29/4427* (2013.01); *F05D 2260/80* (2013.01); *F05D 2260/83* (2013.01); *F05D 2270/333* (2013.01); *G01N 2291/0289* (2013.01); *G01N 2291/2693* (2013.01)

(58) Field of Classification Search
CPC .... F04D 29/324; F04D 29/522; F04D 29/542; G01N 29/0654; G01N 29/265; G01N 2291/2693; F05D 2260/83; G01H 9/00; G01H 1/00; G01H 3/00
See application file for complete search history.

(56) References Cited

U.S. PATENT DOCUMENTS

| | | | |
|---|---|---|---|
| 2009/0055071 A1* | 2/2009 | Way | F02C 9/28 701/100 |
| 2012/0099735 A1* | 4/2012 | Chen | G02B 23/2476 381/56 |

FOREIGN PATENT DOCUMENTS

| | | | | |
|---|---|---|---|---|
| WO | WO 2015092221 | * | 6/2015 | ........... H04N 5/2256 |
| WO | WO 2015092221 A1 | | 6/2015 | |

* cited by examiner

METHOD FOR CARRYING OUT A SOUND TEST OF ATLEAST ONE COMPONENT AND ENDOSCOPE DEVICE USED FOR THE SAME

CROSS-REFERENCE TO RELATED APPLICATION

This application claims priority to German Application No. 10 2016 203 904.0 having a filing date of Mar. 10, 2016 the entire contents of which are hereby incorporated by reference.

FIELD OF TECHNOLOGY

The following relates to a method for carrying out a sound test for detecting and/or analyzing material faults and/or mounting faults of at least one component, in which the component is excited, by striking, to experience vibrations which generate soundwaves, after which the generated soundwaves are detected and conclusions are drawn about material faults and/or mounting faults on the basis of the detected soundwaves. In addition, embodiments of the present invention relates to an endoscope device which has at least one handling unit and a shaft which is connected thereto and is of rigid or flexible design and in which an image transmission device and a light transmission device are integrated in such a way that image signals and light signals can be transmitted from the free end of the shaft to the handling unit.

BACKGROUND

Methods for carrying out a sound test for detecting and/or analyzing material faults and/or mounting faults of components are already known. In order to evaluate deviations of a turbine blade with respect to the delivery state or design state, for example with respect to the tensioning of the blades, loosening of the attachment of the blades or the presence of fractures etc., for example the turbine blade is struck with a hammer when the turbine housing is open, and the resulting sound pattern is analyzed acoustically by trained and very experienced personnel without technical aids. This requires many years of experience in order to be able to differentiate "good" sound patterns from "bad" sound patterns. A problem when carrying out such a sound test is that when checking very inaccessibly arranged components said sound test involves a very large amount of expenditure since the components have to be made accessible for the implementation of the hammer blow. It is also problematic that the evaluation result has hitherto been of a subjective nature and therefore very susceptible to errors. Furthermore, for economic grounds it would be advantageous for such a sound test also to be able to be carried out by less experienced personnel.

In addition, endoscopes of the type mentioned at the beginning are known. They have been successfully used for many years in the field of technology for inspecting optically components which are difficult to access, without having to carry out costly disassembly operations. In particular rigid endoscopes and flexible endoscopes are contemporary types of endoscopes, wherein the so-called video endoscopes form a subgroup of the flexible endoscopes. All the endoscopes have in common the fact that they form a handling unit which, in the case of a rigid endoscope, is connected to a rigid shaft, and in the case of a flexible endoscope is connected to a shaft which is of flexible design. An image transmission device and a light transmission device are integrated into the shaft in such a way that image signals and light signals can be transmitted from the free end of the shaft to the handling unit. The image transmission device can be formed by a lens arrangement and an eyepiece which is arranged on the handling unit. Alternatively, as in the case of the video endoscope for the generation of images and transmission of images it is also possible to use digital technology with which video images can be displayed on a monitor which is either provided separately or attached to the handling unit. The image transmission device is nowadays implemented by a light guide fiber bundles which are arranged in the shaft and by which light which is emitted by a light source usually integrated into the handling unit is guided to the free end of the shaft.

Furthermore, the use of endoscopes is known with gripping tools and cutting tools in the medical field, for example for the removal of tissue samples or the like.

Taking this known art as a starting point, a purpose of the embodiments of the present invention is to make available an improved method of the type mentioned at the beginning with which sound tests for detecting and/or analyzing material faults and/or mounting faults can be carried out without difficulty and cost-effectively even on components which are difficult to access. In addition, a purpose of the embodiments of the present invention is to make available technical means for carrying out such a method.

SUMMARY

An aspect relates to a method of the type specified at the beginning which is characterized in that the striking of the component and the detection of the vibrations are carried out using an endoscope device. In this way it is possible to carry out a sound test method even with components which are difficult to access, without having to expose these components in advance. Correspondingly, the method according to embodiments of the invention involves only a very low level of expenditure.

According to one refinement of the present invention, the at least one component is a component which is arranged inside a housing, in particular a guide blade or a rotor blade arranged inside a turbine housing or compressor housing, wherein the method is carried out with the housing closed.

According to an alternative refinement of the embodiments of the present invention, the at least one component is a guide blade or rotor blade arranged inside a housing lower part of a turbine housing or compressor housing which is divided into a housing upper part and a housing lower part, wherein the method is carried out in a state in which the housing upper part is taken off and a rotor is arranged in the housing lower part.

According to a first variant of the method according to embodiments of the invention, the detected vibrations are output via a loudspeaker and subsequently analyzed manually by trained personnel for the detection and/or analysis of material faults and/or mounting faults of the component, without further technical aids.

According to one alternative variant, the detected vibrations are transmitted to an evaluation device and compared therein automatically for the detection and/or analysis of material faults and/or mounting faults of the component with reference values stored in the evaluation device. The second variant is distinguished compared to the first variant in particular in that the degree of training of the personnel carrying out the method can be significantly lower.

In order to solve the problem mentioned at the beginning, embodiments of the present invention also provide an endoscope device of the type mentioned at the beginning which is characterized in that a pulse generator which can be activated by means of the handling unit is formed in the shaft in such a way that when it is activated a component which is present in the region of the free end of the shaft can be struck. Thanks to such a pulse generator, the endoscope device according to embodiments of the invention can be used to carry out sound tests of the type mentioned at the beginning, in particular on components which are difficult to access.

According to one refinement of the embodiments of the present invention, a sensor device is provided in the region of the free end of the shaft and is formed in such a way that it generates signals representing received soundwaves and transmits them to a handling unit. Alternatively, such a sensor device can, however, also be provided in the region of a free end of a shaft of a separate endoscope device.

The image transmission device, the light transmission device and, if appropriate the sensor device are advantageously arranged in channels which are separate from one another and extend through the shaft. This provides a very simple design.

The image transmission device is advantageously provided in the form of a camera system, and the endoscope device is therefore configured in the manner of a video endoscope. On the one hand, this simplifies the handling of the endoscope device. However, on the other hand, the image data can also be stored.

According to one refinement of the embodiments of the present invention, the pulse generator has a firing pin which can be activated, in particular, mechanically, pneumatically or electromechanically, preferably by means of the handling unit. By means of such a firing pin and corresponding activation, very uniform striking of components can be ensured. The impetus of the firing pin can also be set very precisely, with the result that it can be adapted to a wide variety of materials for testing the components.

The sensor device advantageously has a microphone, a laser vibrometer or an acceleration pickup. In this way, the soundwaves which originate from a struck component can be detected and received in a simple and economical fashion. However, it should be clear that basically other forms of solid-borne sound measurements are also possible such as, for example, by means of travel measuring methods or speed measuring methods.

According to one refinement of the embodiments of the present invention, an evaluation device is provided which is configured in such a way that it evaluates signals representing soundwaves transmitted by the sensor device, in particular compares the signal spectrum and/or impulse response of said signals with reference values stored in the evaluation device. Thanks to such a refinement, the evaluation of the signals can be automated completely or at least partially, with the result that there is no need for particularly intensive training of the personnel.

The evaluation device is advantageously arranged on the handling device or integrated therein, as a result of which a compact endoscope device is obtained.

BRIEF DESCRIPTION

Some of the embodiments will be described in detail, with reference to the following figures, wherein like designations denote like members, wherein.

Figure 9:
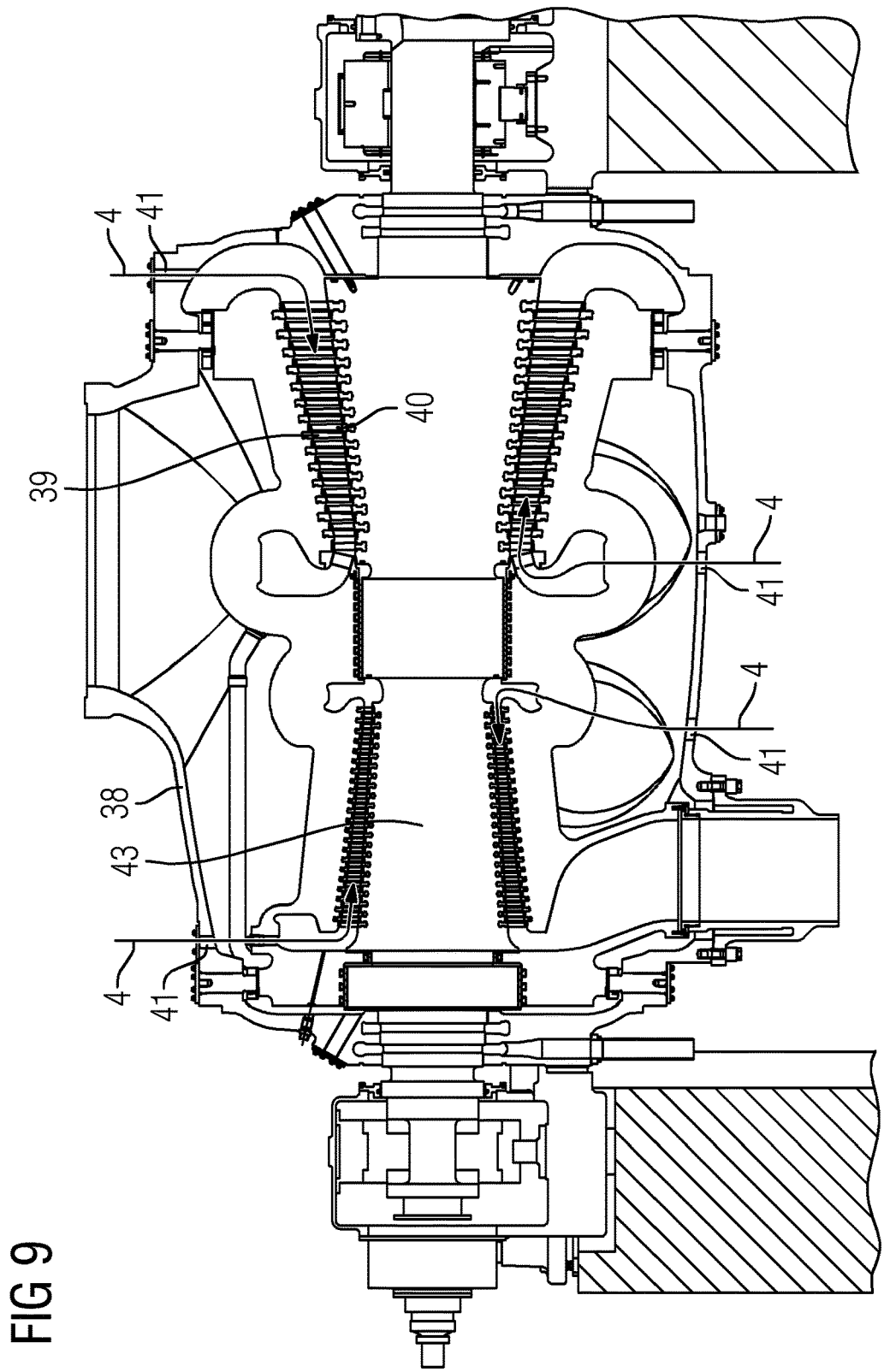
Figure 10:
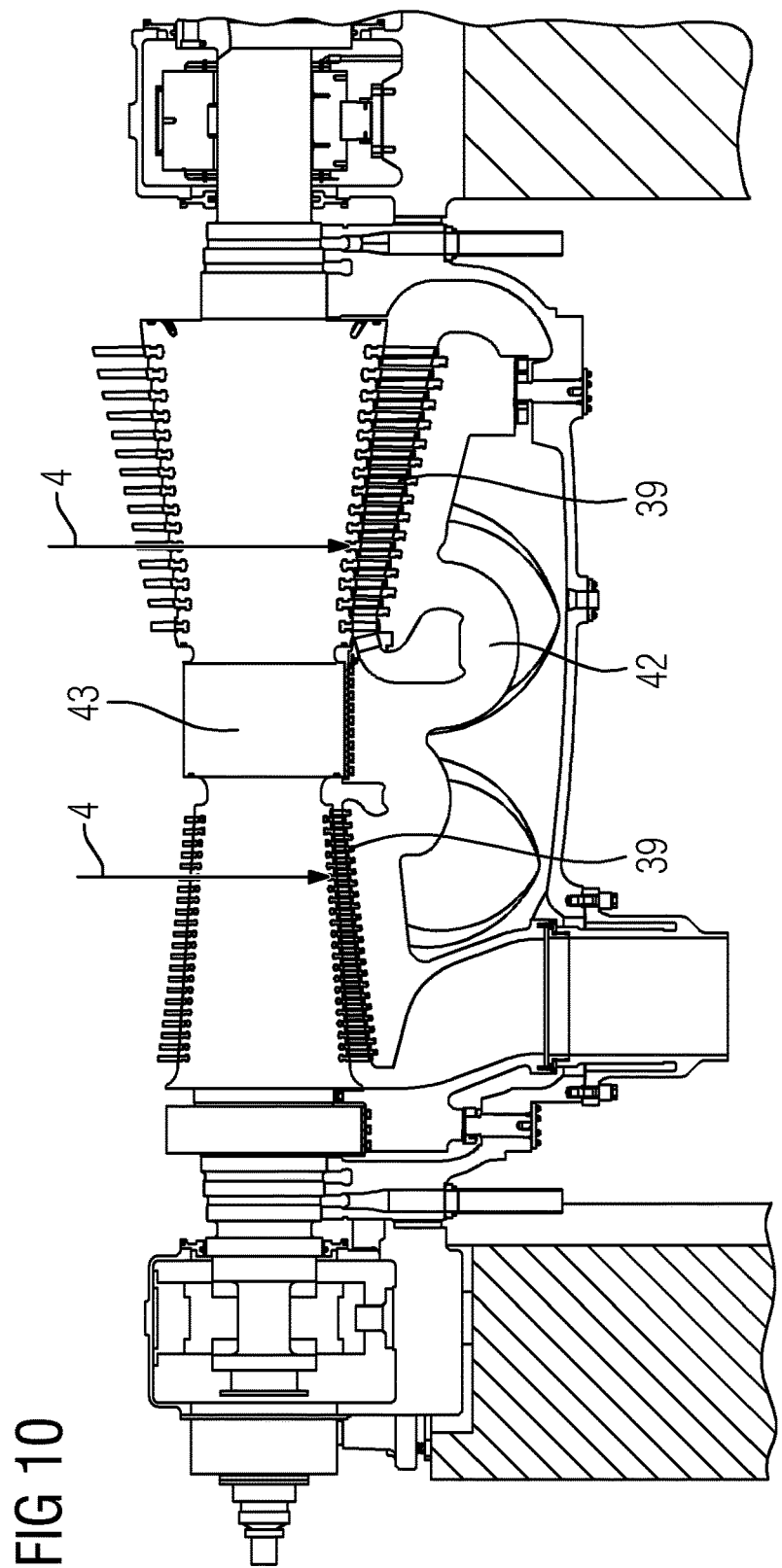

FIG. 9 shows a schematic sectional view through a turbine on the basis of which a method according to an embodiment of the present invention is described using an endoscope device; and FIG. 10 shows a schematic sectional view of a turbine of a jointed design in which an upper housing half is removed, in which a rotor is arranged in a lower housing half, and on the basis of which a method according to a further embodiment of the present invention is described using an endoscope device according to embodiments of the invention.

DETAILED DESCRIPTION

Figure 1:
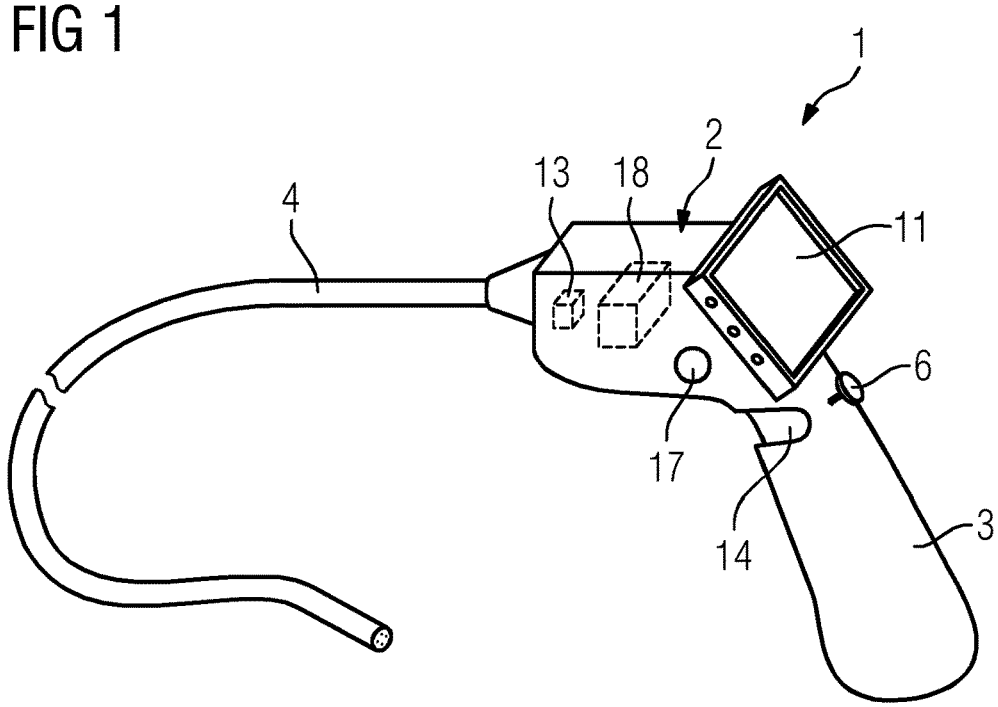
FIG. 1 shows a schematic view of an endoscope device according to an embodiment of the present invention.
Figure 2:
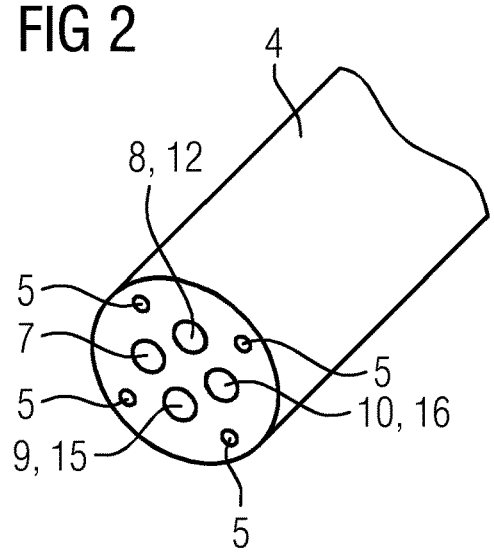
FIG. 2 shows a schematic view of a free end of a shaft of the endoscope device illustrated in FIG. 1.

FIG. 1 shows an endoscope device 1 according to an embodiment of the present invention. The endoscope device 1 comprises a handling unit 2 which is defined on the outside by a housing which defines a grip region 3, and a shaft 4 which is embodied in a flexible way here. Within the shaft 4, Bowden cables 5 are arranged in a known fashion, which Bowden cables 5 can be activated in order to move the shaft 4 by means of the handling unit 2, here by means of a switching lever 6 which is arranged on the handling unit 2 and can move in all directions. In addition to the Bowden cables 5, an image transmission device 7, a light transmission device 8, a pulse generator 9 and a sensor device 10 are integrated into the shaft 4, which image transmission device 7, light transmission device 8, pulse generator 9 and sensor device 10 are each arranged in the present exemplary embodiment in channels which are separate from one another and which extend through the shaft 4 from the handling unit 2 as far as the free end of the shaft 4. However, it should be clear that it is basically also possible to arrange at least some of the specified components in a common channel, such as, for example, the image transmission device 7 and the light transmission device 8.

The image transmission device 7 is embodied here in such a way that image signals are transmitted from the free end of the shaft 4 to a monitor 11 arranged on the handling unit 2, in the manner of a video endoscope. Even if a digital image transmission is preferred, it is alternatively also possible to implement the image transmission device optically, for example by means of a lens system and an eyepiece which is arranged on the handling unit 2, in particular when the shaft 4 is embodied as a rigid shaft.

The light transmission device 8 comprises here a glass fiber cable bundle 12 which guides light from a light source 13 which is positioned within the handling unit 2 and is embodied here as an LED light source, to the free end of the shaft 4.

The pulse generator 9 is embodied in such a way that when it is activated the switches 14 which are provided on the handling unit 2 can be struck by means of a component which is provided in the region of the free end of the shaft 4, as is also explained in more detail below with reference to FIG. 9. The pulse generator 9 has for this purpose a firing pin 15 which can be activated pneumatically or electromagnetically or else mechanically depending on the design. These examples of the implementation unit of the various types of activation are illustrated in FIGS. 3 to 8, to which reference is made in more detail below.

The sensor device 10 is embodied in such a way that it generates signals representing received soundwaves and transmits them to the handling unit 2. For this purpose, the sensor device 10 has here a microphone 16 which transmits received signals to a loudspeaker 17 which is provided on the handling unit 2. Alternatively, the signals can, however, also be transmitted to an evaluation device 18 which is also integrated here into the handling unit 2, but can alternatively also be provided separately. The evaluation device 18 is configured in such a way that it evaluates signals representing soundwaves transmitted by the sensor device 10 by comparing the signal strength of said signals with, in particular, reference values stored in the evaluation device 18. At this point it is to be noted that instead of a microphone 16, the sensor device 10 can also have other suitable sensors, in particular in the form of a laser vibrometer, an acceleration pickup or the like.

Figure 3:
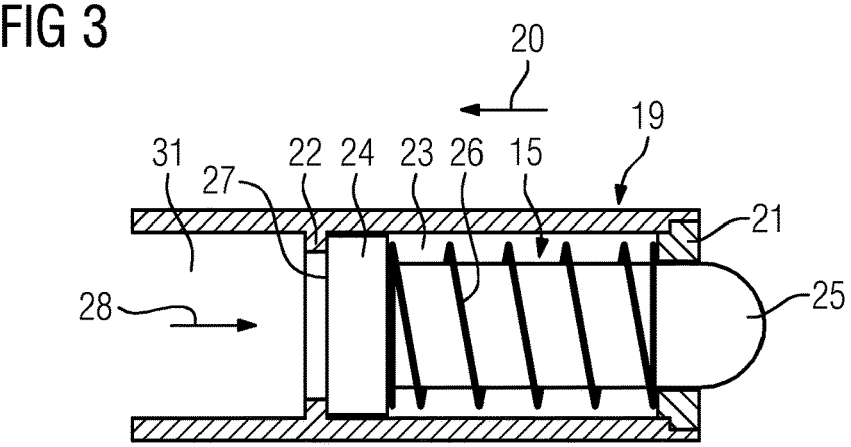
FIG. 3 shows a schematic sectional view through a pneumatically activated pulse generator of the endoscope device illustrated in FIG. 1.
Figure 4:
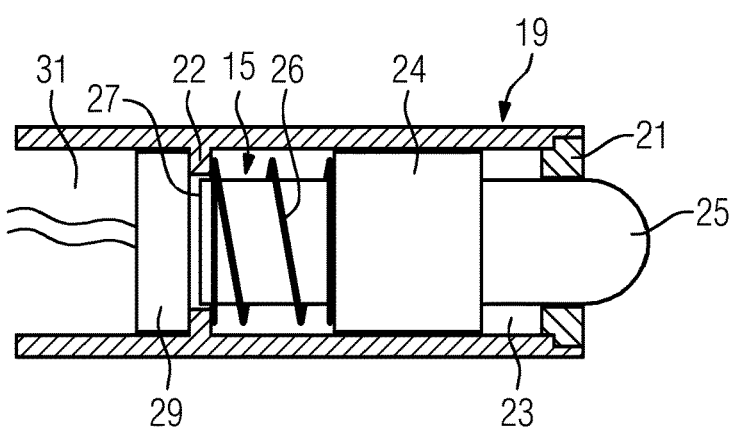
FIG. 4 shows a schematic sectional view through an alternative electromagnetically activated pulse generator according to an embodiment of the present invention.
Figure 5:
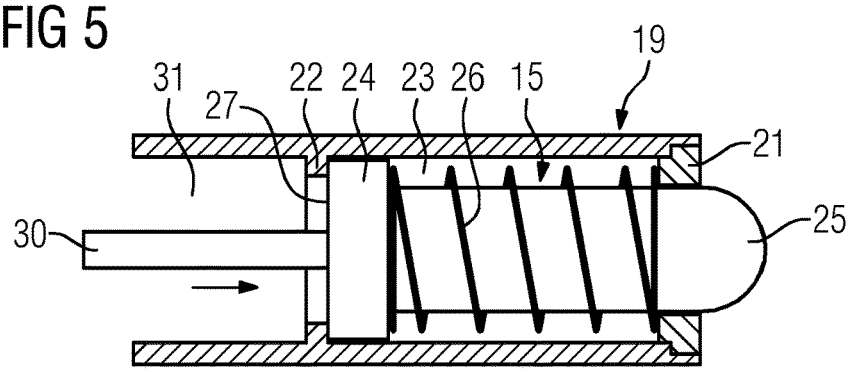
FIG. 5 shows a schematic sectional view through an alternative mechanically activated pulse generator according to an embodiment of the present invention.

FIGS. 3 to 5 show various activation principles of the firing pin 15 of the pulse generator 9.

FIG. 3 shows a sleeve 19 which is inserted into the shaft channel of the pulse generator 9 starting from its free end, in the direction of the arrow 20. The sleeve 19 has two annular projections 21 and 22 which are arranged spaced apart from one another, protrude radially inward and define a receptacle space 23 for the firing pin 15, wherein the annular projection 21 which is provided at the free end is provided here as a separate component, while the other annular projection 22 is embodied in an integral fashion with the sleeve 19. The firing pin 15 is provided at its free end with a radially outwardly protruding annular shoulder 24 and its other free end with a semispherical head 25. Within the receptacle space 23 a pressure spring 26 is accommodated which is supported, on the one hand, against the annular projection 21 and, on the other hand, against the annular shoulder 24 of the firing pin 15. In order to accelerate the firing pin 15 to strike a workpiece in the outward direction, the outer end face 27 of the annular projection 24 of the firing pin 15 can be acted on in the direction of the arrow 28 with compressed air, with the result that the firing pin 15 is moved with a predetermined impulse counter to the restoring force of the compression spring 26.

FIG. 4 shows an electromagnetic variant for activating the firing pin 15. In this variant, the annular shoulder 24 is attached approximately centrally to the firing pin 15, wherein the compression spring 26 which is arranged within the receptacle space 23 is supported against the annular shoulder 24 of the firing pin 15, on the one hand, and against the annular projection 22, on the other. Arranged opposite the firing pin 15 on the other side of the annular projection 22 is an electromagnet which holds the ferromagnetically embodied firing pin 15 counter to the actuating force of the compression spring 26 in the pulled-back position. If the electromagnet is switched off, the compression spring 26 presses against the annular shoulder 24 of the firing pin 15 in such a way that the firing pin 15 shoots forward with a predetermined impetus.

FIG. 5 shows a first embodiment of a mechanically activated firing pin 15. The design illustrated in FIG. 5 corresponds essentially to the design in FIG. 3, only that the firing pin 25 is not activated by means of compressed air but instead by means of a wire 30 with which the firing pin 15 can be pressed outward with a predetermined impetus counter to the restoring force of the compression spring 26.

Figure 6:
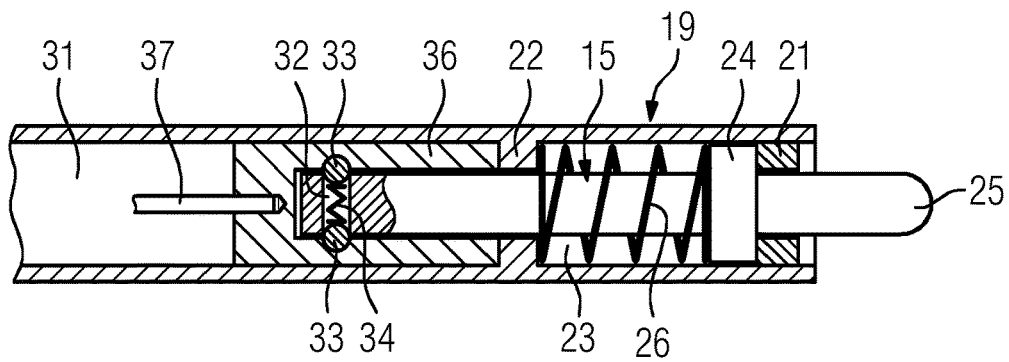
FIG. 6 shows schematic sectional views which show a further design of a mechanically activated pulse generator in various operating positions.
Figure 7:
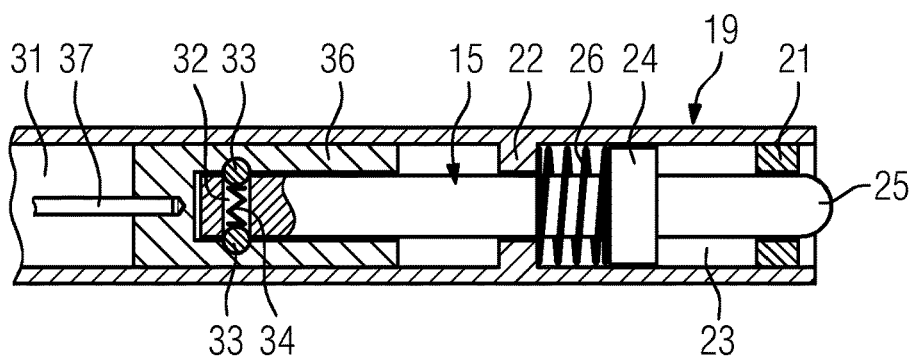
FIG. 7 shows schematic sectional views which show a further design of a mechanically activated pulse generator in various operating positions.
Figure 8:
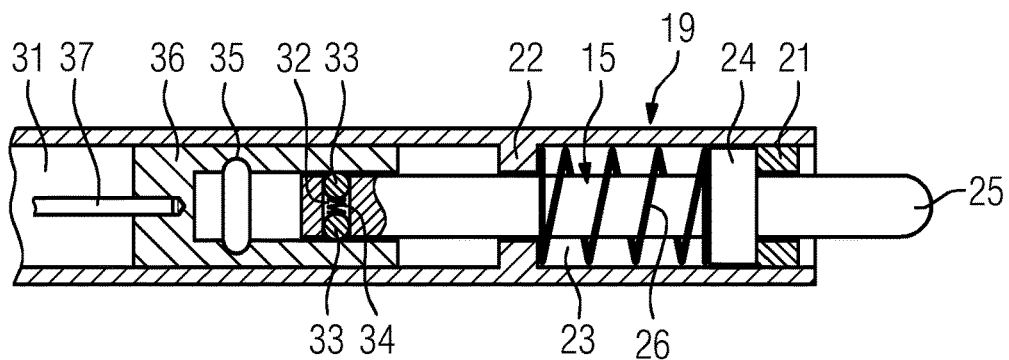
FIG. 8 shows schematic sectional views which show a further design of a mechanically activated pulse generator in various operating positions.

FIGS. 6 to 8 show a second variant of a mechanically activated firing pin 15 in various positions. In this variant, the compression spring 26 is supported between the annular projection 22 and the annular shoulder 24 which is arranged in the front half of the firing pin 15. The rear end of the firing pin 15 which extends beyond the annular projection is arranged in a rear receptacle space 31 of the sleeve 19 and has a radially extending drilled hole 32 in which two spheres 33 which lie opposite each other are accommodated which engage radially outward, via a spring 34 arranged between the spheres 33, into an annular groove 35 of a guide element 36 which engages around the free end of the firing pin 15 and is accommodated in an axially movable fashion within the rear receptacle space 31 of the sleeve 19. A wire 37 which extends as far as the handling unit 2 is secured to the free end of the guide element 36. In the relaxed state, illustrated in FIG. 6, the compression spring 26 presses the annular shoulder 24 of the firing pin 15 against the annular projection 21. In order to tension the system, the wire 37 is pulled back counter to the restoring force of the compression spring 26 according to FIG. 7 as long as the spring force of the spring 34 is sufficiently large in order to maintain the connection between the firing pin 15 and the guide element 36 via the spheres 33. If the spring force of the compression spring 26 exceeds the horizontal force component between the spheres 33 and the guide element 36, the connection between the firing pin 15 and the guide element 36 is released, after which the firing pin 15 is accelerated impulsively as far as the annular projection 21 by the restoring force of the compression spring 26.

A method for carrying out a sound test for detecting and/or analyzing material faults and/or mounting faults of guide or rotor blades 39, 40 arranged within a turbine housing 38 using an endoscope device 1 of the type described above is described below with reference to FIG. 9. For this purpose, the shaft 4 of the endoscope device 1 is introduced through an already present or additionally provided flange opening 41 in the turbine housing 38 and pushed forward as far as the guide blade 39 or rotor blade 40 which is to be tested. As soon as the free end of the shaft 4 comes into contact with the guide blade 39 or rotor blade 40 which is to be tested, the firing pin 15 is activated, depending on the embodiment variant of the endoscope device 1, pneumatically, electromagnetically or mechanically by means of the switch 14, in such a way that the blade is excited to experience vibrations which generate soundwaves. The vibrations are then detected by means of the sensor device 10, after which conclusions are drawn about the material fault and/or mounting fault on the basis of the detected soundwaves. The detection of the soundwaves can be carried out, for example, by means of the microphone 16, after which the detected soundwaves are output via the loudspeaker 17 and are then analyzed by trained personnel without further technical aids. Alternatively, the detected soundwaves can, however, also be conveyed to the evaluation device 18 within which the analysis takes place automatically by comparing the signals representing the detected soundwaves with limiting values stored within the evaluation device 18.

The method described above is distinguished, in particular, by virtue of the fact that a sound test can be carried out on the guide blade 39 and rotor blade 40 without previously exposing the guide blade 39 and rotor blade 40, that is to say without having to disassemble the turbine housing 38. Correspondingly, the method according to embodiments of the invention can also be carried out quickly and economically without a large amount of expenditure.

It is to be noted that the sensor device 10 can basically also be arranged on a separate endoscope device (not illustrated here). In this case, the previously described method is carried out by guiding the shafts of the two endoscope devices into the region of the blade to be tested.

FIG. 10 shows the execution of the previously described method in a turbine housing 38 of a jointed design which is divided into a housing upper part and a housing lower part 42, wherein the housing upper part which is not illustrated here is taken off the housing lower part 42, and the rotor 43 is still arranged on the housing lower part 42. Here, thanks to the use of the endoscope device 1 it is possible to dispense at least with the removal of the rotor 43.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. A method for carrying out a sound test for detecting and analyzing material faults and mounting faults of at least one component, in which the component is excited, by striking, to experience vibrations which generate soundwaves, after which the generated soundwaves are detected and conclusions are drawn about at least one of material faults and at least one of mounting faults on the basis of the detected soundwaves, wherein the striking of the component and the detection of the vibrations are carried out using an endoscope device, wherein the striking of the component is activated by means of a handling unit of the endoscope device.

2. The method as claimed in claim 1, wherein the at least one component is a component which is arranged inside a housing, in particular a guide blade or rotor blade arranged inside a turbine housing or compressor housing, and in that the method is carried out with a closed housing.

3. The method as claimed in claim 1, wherein the at least one component is a guide blade or rotor blade arranged inside a housing lower part of a turbine housing or compressor housing which is divided into a housing upper part and a housing lower part, and in that the method is carried out in a state in which the housing upper part is taken off and a rotor is arranged in the housing lower part.

4. The method as claimed in claim 1, wherein the detected vibrations are output via a loudspeaker and subsequently analyzed manually by trained personnel for at least one of the detection and analysis of at least one of material faults and mounting faults of the component, without further technical aids.

5. The method as claimed in claim 1, wherein the detected vibrations are transmitted to an evaluation device and compared therein automatically for the at least one of the detection and analysis of at least one of material faults and at least one of mounting faults of the component with reference values stored in the evaluation device.

6. The endoscope device, in which the endoscope device has at least one handling unit and a shaft which is connected thereto and is of rigid or flexible design and in which an image transmission device and a light transmission device are integrated in such a way that the image signals and light signals can be transmitted from the free end of the shaft to the handling unit, wherein a pulse generator which can be activated by the handling unit is formed in the shaft in such a way that when it is activated a component which is present in the region of the free end of the shaft can be struck.

7. The endoscope device as claimed in claim 6, wherein a sensor device is provided in the region of the free end of the shaft and is formed in such a way that it generates signals representing received soundwaves and transmits them to the handling unit.

8. The endoscope device as claimed in claim 6, wherein the image transmission device, the light transmission device and the sensor device are arranged in channels which are separate from one another and extend through the shaft as far as the free end of the shaft.

9. The endoscope device as claimed in claim 6, wherein the image transmission device is provided in the form of a camera system.

10. The endoscope device as claimed in claim 6, wherein the pulse generator has a firing pin which can be activated mechanically, pneumatically or electromechanically, by the handling unit.

11. The endoscope device as claimed in claim 6, wherein the sensor device has a microphone, a laser vibrometer or an acceleration pickup.

12. The endoscope device as claimed in claim 6, wherein an evaluation device is provided which is configured in such a way that it evaluates signals representing soundwaves transmitted by the sensor device, and compares a signal spectrum and impulse response of said signals with reference values stored in the evaluation device.

13. The endoscope device as claimed in claim 12, wherein the evaluation device is arranged on the handling device or integrated therein.

* * * * *